United States Patent
Dawson

(10) Patent No.: US 6,399,608 B1
(45) Date of Patent: Jun. 4, 2002

(54) COMBINATION OF A GABA-$_A$ α 2/3 AGONIST AND A SELECTIVE SEROTONIN REUPTAKE INHIBITOR

(75) Inventor: Gerard Raphael Dawson, Saffron Walden (GB)

(73) Assignee: Merck Sharp & Dohme Ltd., Hoddesdon (GB)

( * ) Notice: Subject to any disclaimer, the term of this patent is extended or adjusted under 35 U.S.C. 154(b) by 0 days.

(21) Appl. No.: 09/600,672

(22) PCT Filed: Jan. 19, 1999

(86) PCT No.: PCT/GB99/00161

§ 371 (c)(1),
(2), (4) Date: Jul. 20, 2000

(87) PCT Pub. No.: WO99/37303

PCT Pub. Date: Jul. 29, 1999

(30) Foreign Application Priority Data

Jan. 23, 1998 (GB) ............................................... 9801538

(51) Int. Cl.$^7$ ................. A61K 31/5025; A61K 31/451; A61K 31/4525; A61K 31/135; A61K 31/138
(52) U.S. Cl. ...................... 514/248; 514/321; 514/647; 514/651
(58) Field of Search ............................... 514/248, 647, 514/321, 649, 651

(56) References Cited

U.S. PATENT DOCUMENTS

| | | | |
|---|---|---|---|
| 4,112,095 A | 9/1978 | Allen, Jr. et al. | 424/250 |
| 4,117,130 A | 9/1978 | Allen, Jr. et al. | 424/250 |
| 4,230,705 A | 10/1980 | Allen, Jr. et al. | 424/250 |
| 4,260,755 A | 4/1981 | Moran et al. | 544/236 |
| 4,260,756 A | 4/1981 | Moran et al. | 544/236 |
| 4,654,343 A | 3/1987 | Albright et al. | 514/248 |

FOREIGN PATENT DOCUMENTS

| | | |
|---|---|---|
| DE | 27 41 763 | 9/1977 |
| EP | 0 085 840 | 8/1983 |
| EP | 0 134 946 | 3/1985 |
| WO | WO 98/04559 | 2/1998 |

OTHER PUBLICATIONS

Bayley, et al., J. Psychopharmacol., 10:26–213 (1996).
Bristow, et al., J. Pharmacol. Exp. Ther., 279: 492–501 (1996).
Dawson, et al., Psychoparmacology, 121: 109–117 (1995).
Wafford, et al., Mol. Pharmacol., 50: 670–678 (1996).
Delini–Stula, et al., J. psychiat. Res., 30:239–250 (1996).
Hadingham, et al., Mol. Pharmacol., 43:970–975 (1993).
Hall, et al., J. Cereb. Blood Flow Metab., 17:875–882 (1997).
Handley, et al., CNS Drugs. 2(S): 397–414 (1994).
Smith, R.C., et al., Psychopharmacol. Bull., 32:518 (1996).
Smith, W.T., et al., Psychopharmacol. Bull., 32:519 (1996).
Sussman, et al., J. Clin. Psychiatry, 59:42–48 (1998).
Tarzia, et al., II Farmaco—Ed. Sc., 43:189–201 (1987).

Primary Examiner—Phyllis G. Spivack
(74) Attorney, Agent, or Firm—J. Eric Thies; Shu M. Lee; Melvin Winokur

(57) ABSTRACT

A pharmaceutical product comprising an SSRI and a non-sedating anxiolytic compound, which is a modulator of the benzodiazepine binding site of the human GABA$_A$ receptor, having a binding affinity for the α3 subunit of the human GABA$_A$ receptor of 10 nM or less, which elicits at least a 40% potentiation of the GABA EC$_{20}$ response in stably transfected recombinant cell lines expressing the α3 subunit of α3 and which elicits at most a 30% potentiation of the GABA EC$_{20}$ response in stably transfected cell lines expressing the α1 subunit of the human GABA$_A$ receptor is disclosed for simultaneous, separate or sequential administration.

14 Claims, No Drawings

COMBINATION OF A GABA-$_A$ α 2/3 AGONIST AND A SELECTIVE SEROTONIN REUPTAKE INHIBITOR

This is an application under 35 U.S.C. 371 of PCT/GB99/00161 and claims priority from Great Britain Application No. 9801538.1, filed Jan. 23, 1998.

The present invention relates to a pharmaceutical product comprising a GABA$_A$ α2/3 agonist and an SSRI.

Selective serotonin reuptake inhibitors (SSRIs) are a new class of antidepressant drugs.

Receptors for the major inhibitory neurotransmitter, gamma-aminobutyric acid (GABA), are divided into two main classes: (1) GABA$_A$ receptors, which are members of the ligand-gated ion channel superfamily; and (2) GABA$_B$ receptors, which may be members of the G-protein linked receptor superfamily. Since the first cDNAs encoding individual GABA$_A$ receptor subunits were cloned the number of known members of the mammalian family has grown to thirteen (six α subunits, three β subunits, three γ subunits and one δ subunit). It may be that further subunits remain to be discovered; however, none has been reported since 1993.

Although knowledge of the diversity of the GABA$_A$ receptor gene family represents a huge step forward in our understanding of this ligand-gated ion channel, insight into the extent of subtype diversity is still at an early stage. It has been indicated that an α subunit, a β subunit and a γ subunit constitute the minimum requirement for forming a fully functional GABA$_A$ receptor expressed by transiently transfecting cDNAs into cells. As indicated above, a δ subunit also exists, but is present only to a minor extent in GABA$_A$ receptor populations.

Studies of receptor size and visualisation by electron microscopy conclude that, like other members of the ligand-gated ion channel family, the native GABA$_A$ receptor exists in pentameric form. The selection of at least one α, one β and one γ subunit from a repertoire of thirteen allows for the possible existence of more than 10,000 pentameric subunit combinations. Moreover, this calculation overlooks the additional permutations that would be possible if the arrangement of subunits around the ion channel had no constraints (i.e. there could be 120 possible variants for a receptor composed of five different subunits).

Receptor subtype assemblies which do exist include, amongst many others, α1β2γ2, α2β2/3γ2, α3βγ2/3, α2βγ1, α5β3γ2/3, α6βγ2, α6βδ and α4βδ. Subtype assemblies containing an α1 subunit are present in most areas of the brain and are thought to account for over 40% of GABA$_A$ receptors in the rat. Subtype assemblies containing α2 and α3 subunits respectively are thought to account for about 25% and 17% of GABA$_A$ receptors in the rat. Subtype assemblies containing an α5 subunit are expressed predominantly in the hippocampus and cortex and are thought to represent about 4% of GABA$_A$ receptors in the rat.

A characteristic property of all known GABA$_A$ receptors is the presence of a number of modulatory sites, one of which is the benzodiazepine (BZ) binding site. The BZ binding site is the most explored of the GABA$_A$ receptor modulatory sites, and is the site through which anxiolytic drugs such as diazepam and temazepam exert their effect. Before the cloning of the GABA$_A$ receptor gene family, the benzodiazepine binding site was historically subdivided into two subtypes, BZ1 and BZ2, on the basis of radioligand binding studies. The BZ1 subtype has been shown to be pharmacologically equivalent to a GABA$_A$ receptor comprising the α1 subunit in combination with a β subunit and γ2. This is the most abundant GABA$_A$ receptor subtype, and is believed to represent almost half of all GABA$_A$ receptors in the brain.

Two other major populations are the α2βγ2 and α3βγ2/3 subtypes. Together these constitute approximately a further 35% of the total GABA$_A$ receptor repertoire. Pharmacologically this combination appears to be equivalent to the BZ2 subtype as defined previously by radioligand binding, although the BZ2 subtype may also include certain α5-containing subtype assemblies. The physiological role of these subtypes has hitherto been unclear because no sufficiently selective agonists or antagonists were known.

It is now believed that agents acting as BZ agonists at α1βγ2, α2βγ2, or α3 βγ2 subunits will possess desirable anxiolytic properties. Compounds which are modulators of the benzodiazepine binding site of the GABA$_A$ receptor by acting as BZ agonists are referred to hereinafter as "GABA$_A$ receptor agonists". The α1-selective GABA$_A$ receptor agonists alpidem and zolpidem are clinically prescribed as hypnotic agents, suggesting that at least some of the sedation associated with known anxiolytic drugs which act at the BZ1 binding site is mediated through GABA$_A$ receptors containing the α1 subunit. Accordingly, it is considered that GABA$_A$ receptor agonists which bind more effectively to the α2 and/or α3 subunit than to α1 will be effective in the treatment of anxiety with a reduced propensity to cause sedation. Also, agents which are antagonists or inverse agonists at α1 might be employed to reverse sedation or hypnosis caused by α1 agonists.

The products of the present invention are of use in the treatment and/or prevention of a variety of disorders of the central nervous system. Such disorders include anxiety disorders, such as panic disorder with or without agoraphobia, agoraphobia without history of panic disorder, animal and other phobias including social phobias, obsessive-compulsive disorder, stress disorders including post-traumatic and acute stress disorder, and generalized or substance-induced anxiety disorder; neuroses; convulsions; migraine; and depressive or bipolar disorders, for example single-episode or recurrent major depressive disorder, dysthymic disorder, bipolar I and bipolar II manic disorders, and cyclothymic disorder.

In DE-A-2741763, and in U.S. Pat. Nos. 4,260,755, 4,260,756 and 4,654,343, are described various classes of 1,2,4-triazolo[4,3-b]pyridazine derivatives which are alleged to be useful as anxiolytic agents. The compounds described in DE-A-2741763 and in U.S. Pat. Nos. 4,260,755 and 4,654,343 possess a phenyl substituent at the 6-position of the triazolo-pyridazine ring system. The compounds described in U.S. Pat. No. 4,260,756, meanwhile, possess a heteroaryl moiety at the 6- or 8-position. In none of these publications, however, is there any disclosure or suggestion of 1,2,4-triazolo[4,3-b]pyridazine derivatives wherein the substituent at the 6-position is attached through a directly linked oxygen atom.

EP-A-0085840 and EP-A-0134946 describe related series of 1,2,4-triazolo[3,4-a]phthalazine derivatives which are stated to possess antianxiety activity. However, there is no disclosure nor any suggestion in either of these publications of replacing the benzo moiety of the triazolo-phthalazine ring system with any other functionality.

The present invention utilises a class of triazolo-pyridazine derivatives which possess desirable binding properties at various GABA$_A$ receptor subtypes. The GABA compounds of use in the present invention have good affinity as ligands for the α2 and/or α3 subunit of the human GABA$_A$ receptor. The GABA compounds of use in this invention may display more effective binding to the α2 and/or α3 subunit than to the α1 subunit. Desirably, the GABA compounds of use in the invention will exhibit functional selectivity in terms of a selective efficacy for the α2 and/or α3 subunit relative to the α1 subunit.

The GABA compounds of use in the present invention are GABA$_A$ receptor subtype ligands having a binding affinity ($K_i$) for the α2 and/or α3 subunit, as measured in the assay described hereinbelow, of 100 nM or less, typically of 50 nM or less, and ideally of 10 nM or less. The GABA compounds of use in accordance with this invention may possess at least a 2-fold, suitably at least a 5-fold, and advantageously at least a 10-fold, selective affinity for the α2 and/or α3 subunit relative to the α1 subunit. However, compounds which are unselective in terms of their binding affinity for the α2 and/or α3 subunit relative to the α1 subunit are also of use in the present invention; such compounds will desirably exhibit functional selectivity in terms of a selective efficacy for the α2 and/or α3 subunit relative to the α1 subunit.

The products of the present invention have the advantage that they surprisingly provide relief from anxiety more rapidly than would be expected from the administration of either compound alone.

The present invention thus provides a pharmaceutical product comprising an SSRI and a compound of formula I, or a salt or prodrug thereof:

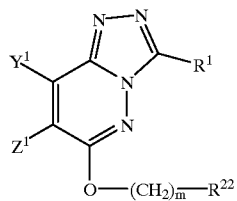

(I)

wherein $Y^1$ represents hydrogen or methyl;

$Z^1$ represents $C_{1-6}$ alkyl, $C_{3-7}$ cycloalkyl, $C_{4-7}$ cycloalkenyl, aryl, $C_{3-7}$ heterocycloalkyl, heteroaryl or di($C_{1-6}$)alkylamino, any of which groups may be optionally substituted;

$R^1$ represents $C_{3-7}$ cycloalkyl, phenyl, furyl, thienyl or pyridinyl, any of which groups may be optionally substituted;

m is 1 or 2, preferably 1; and $R^{22}$ represents aryl or heteroaryl, either of which groups may be optionally substituted.

The present invention also provides a compound of formula I as defined above, or a salt or prodrug thereof, wherein $Z^1$ represents $C_{1-6}$ alkyl, $C_{3-7}$ cycloalkyl, aryl, $C_{3-7}$ heterocycloalkyl, or heteroaryl, any of which groups may be optionally substituted; and $Y^1$, $R^1$, m and $R^{22}$ are as defined above.

The groups $Z^1$, $R^1$ and $R^{22}$ may be unsubstituted, or substituted by one or more, suitably by one or two, substituents. In general, the groups $Z^1$, $R^1$ and $R^{22}$ will be unsubstituted or monosubstituted. Examples of optional substituents on the groups $Z^1$, $R^1$ and $R^{22}$ include $C_{1-6}$ alkyl, aryl($C_{1-6}$)alkyl, pyridyl($C_{1-6}$)alkyl, halogen, halo($C_{1-6}$) alkyl, cyano, cyano($C_{1-6}$)alkyl, hydroxy, hydroxymethyl, $C_{1-6}$ alkoxy, $C_{3-7}$ cycloalkyl($C_{1-6}$)alkoxy, $C_{3-7}$ cycloalkoxy, amino($C_{1-6}$)alkyl, di($C_{1-6}$)alkylamino($C_{1-6}$)alkyl, di($C_{1-6}$) alkylaminocarbonyl($C_{1-6}$)alkyl, N-($C_{1-6}$)alkylpiperidinyl, pyrrolidinyl($C_{1-6}$)alkyl, piperazinyl($C_{1-6}$)alkyl, morpholinyl ($C_{1-6}$)alkyl, di($C_{1-6}$)alkylmorpholinyl($C_{1-6}$)alkyl and imidazolyl($C_{1-6}$)alkyl. Illustrative substituents include $C_{1-6}$ alkyl, aryl($C_{1-6}$)alkyl, pyridyl($C_{1-6}$)alkyl, halogen, halo($C_{1-6}$)alkyl, cyano, cyano($C_{1-6}$)alkyl, hydroxy, hydroxymethyl, $C_{1-6}$ alkoxy, $C_{3-7}$ cycloalkyl($C_{1-6}$)alkoxy, di($C_{1-6}$) alkylamino($C_{1-6}$)alkyl, di($C_{1-6}$)alkylaminocarbonyl($C_{1-6}$) alkyl, morpholinyl($C_{1-6}$)alkyl and imidazolyl($C_{1-6}$)alkyl. Representative substituents include $C_{1-6}$ alkyl, aryl($C_{1-6}$) alkyl, halogen, cyano, hydroxy, hydroxymethyl, $C_{1-6}$ alkoxy and $C_{3-7}$ cycloalkyl($C_{1-6}$)alkoxy for simultaneous, separate or sequential administration.

As used herein, the expression "$C_{1-6}$ alkyl" includes methyl and ethyl groups, and straight-chained or branched propyl, butyl, pentyl and hexyl groups. Particular alkyl groups are methyl, ethyl, n-propyl, isopropyl, tert-butyl and 1,1-dimethylpropyl. Derived expressions such as "$C_{1-6}$ alkoxy" are to be construed accordingly.

Typical $C_{3-7}$ cycloalkyl groups include cyclopropyl, cyclobutyl, cyclopentyl and cyclohexyl.

The expression "$C_{3-7}$ cycloalkyl($C_{1-6}$)alkyl" as used herein includes cyclopropylmethyl, cyclobutylmethyl, cyclopentylmethyl and cyclohexylmethyl.

Typical $C_{4-7}$ cycloalkenyl groups include cyclobutenyl, cyclopentenyl and cyclohexenyl.

Typical aryl groups include phenyl and naphthyl, preferably phenyl.

The expression "aryl($C_{1-6}$)alkyl" as used herein includes benzyl, phenylethyl, phenylpropyl and naphthylmethyl.

Suitable heterocycloalkyl groups include azetidinyl, pyrrolidinyl, piperidinyl, piperazinyl, morpholinyl and thiomorpholinyl groups.

Suitable heteroaryl groups include pyridinyl, quinolinyl, isoquinolinyl, pyridazinyl, pyrimidinyl, pyrazinyl, quinoxalinyl, furyl, benzofuryl, dibenzofuryl, thienyl, benzthienyl, pyrrolyl, indolyl, pyrazolyl, indazolyl, oxazolyl, isoxazolyl, thiazolyl, isothiazolyl, imidazolyl, benzimidazolyl, oxadiazolyl, thiadiazolyl, triazolyl and tetrazolyl groups.

The expression "heteroaryl($C_{1-6}$)alkyl" as used herein includes furylmethyl, furylethyl, thienylmethyl, thienylethyl, pyrazolylmethyl, oxazolylmethyl, oxazolylethyl, isoxazolylmethyl, thiazolylmethyl, thiazolylethyl, imidazolylmethyl, imidazolylethyl, benzimidazolylmethyl, oxadiazolylmethyl, oxadiazolylethyl, thiadiazolylmethyl, thiadiazolylethyl, triazolylmethyl, triazolylethyl, tetrazolylmethyl, tetrazolylethyl, pyridinylmethyl, pyridinylethyl, pyridazinylmethyl, pyrimidinylmethyl, pyrazinylmethyl, quinolinylmethyl, isoquinolinylmethyl and quinoxalinylmethyl.

The term "halogen" as used herein includes fluorine, chlorine, bromine and iodine, especially fluorine or chlorine.

For use in medicine, the salts of the compounds of formula I will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

The present invention includes within its scope the use of prodrugs of the compounds of formula I above. In general, such prodrugs will be functional derivatives of the compounds of formula I which are readily convertible in vivo into the required compound of formula I. Conventional procedures for the selection and preparation of suitable prodrug derivatives are described, for example, in *Design of Prodrugs*, ed. H. Bundgaard, Elsevier, 1985.

Where the GABA compounds of use in the invention have at least one asymmetric centre, they may accordingly exist as enantiomers. Where the compounds according to the invention possess two or more asymmetric centres, they may additionally exist as diastereoisomers. It is to be understood that all such isomers and mixtures thereof in any proportion are encompassed within the scope of the present invention.

Examples of typical optional substituents on the group $R^1$ include methyl, fluoro and methoxy.

Representative values of $R^1$ include cyclopropyl, phenyl, methylphenyl, fluorophenyl, difluorophenyl, methoxyphenyl, furyl, thienyl, methyl-thienyl and pyridinyl. Particular values include cyclopropyl, phenyl, methylphenyl, fluorophenyl, methoxyphenyl and pyridinyl. More particularly, $R^1$ may represent unsubstituted or mono-substituted phenyl. Most particularly, $R^1$ represents phenyl.

Suitably, $Y^1$ represents hydrogen.

Examples of typical substituents on the group $Z^1$ include $C_{1-6}$ alkyl and halogen, especially methyl or chloro.

Representative values for the group $Z^1$ include methyl, ethyl, isopropyl, tert-butyl, 1,1-dimethylpropyl, methyl-cyclopropyl, cyclobutyl, methyl-cyclobutyl, cyclopentyl, methyl-cyclopentyl, cyclohexyl, cyclobutenyl, phenyl, pyrrolidinyl, methyl-pyrrolidinyl, piperidinyl, morpholinyl, thiomorpholinyl, pyridinyl, furyl, thienyl, chloro-thienyl and diethylamino.

Particular values for the group $Z^1$ include methyl, ethyl, isopropyl, tert-butyl, methyl-cyclopropyl, cyclobutyl, methyl-cyclobutyl, cyclopentyl, methyl-cyclopentyl, cyclohexyl, phenyl, pyrrolidinyl, methyl-pyrrolidinyl, piperidinyl, morpholinyl, thiomorpholinyl, pyridinyl, furyl, thienyl and chloro-thienyl.

A favoured value of $Z^1$ is cyclobutyl.

Examples of typical substituents on the group $R^{22}$ include $C_{1-6}$ alkyl, aryl($C_{1-6}$)alkyl, pyridyl($C_{1-6}$)alkyl, halogen, cyano, cyano($C_{1-6}$)alkyl, hydroxymethyl, $C_{1-6}$ alkoxy, $C_{3-7}$ cycloalkyl($C_{1-6}$)alkoxy, di($C_{1-6}$)alkylamino($C_{1-6}$)alkyl, amino($C_{1-6}$)alkyl, di($C_{1-6}$)alkylaminocarbonyl($C_{1-6}$)alkyl, N-($C_{1-6}$)alkylpiperidinyl, pyrrolidinyl($C_{1-6}$)alkyl, piperazinyl($C_{1-6}$)alkyl and morpholinyl($C_{1-6}$)alkyl. Representative substituents include $C_{1-6}$ alkyl, aryl($C_{1-6}$)alkyl, pyridyl($C_{1-6}$)alkyl, halogen, cyano, cyano($C_{1-6}$)alkyl, hydroxymethyl, $C_{1-6}$ alkoxy, $C_{3-7}$ cycloalkyl($C_{1-6}$)alkoxy, di($C_{1-6}$)alkylamino($C_{1-6}$)alkyl, di($C_{1-6}$)alkylaminocarbonyl($C_{1-6}$)alkyl and morpholinyl($C_{1-6}$)alkyl.

Illustrative values of specific substituents on the group $R^{22}$ include methyl, ethyl, n-propyl, benzyl, pyridinylmethyl, chloro, cyano, cyanomethyl, hydroxymethyl, ethoxy, cyclopropylmethoxy, dimethylaminomethyl, aminoethyl, dimethylaminoethyl, dimethylaminocarbonylmethyl, N-methylpiperidinyl, pyrrolidinylethyl, piperazinylethyl and morpholinylmethyl.

Representative values of specific substituents on the group $R^{22}$ include methyl, ethyl, n-propyl, benzyl, pyridinylmethyl, chloro, cyano, cyanomethyl, hydroxymethyl, ethoxy, cyclopropylmethoxy, dimethylaminomethyl, dimethylaminoethyl, dimethylaminocarbonylmethyl and morpholinylmethyl.

Particular values of $R^{22}$ include cyanophenyl, hydroxymethyl-phenyl, pyrazolyl, dimethyl-pyrazolyl, methyl-isoxazolyl, thiazolyl, methyl-thiazolyl, ethyl-thiazolyl, imidazolyl, methyl-imidazolyl, ethyl-imidazolyl, benzyl-imidazolyl, benzimidazolyl, methyl-oxadiazolyl, triazolyl, methyl-triazolyl, propyl-triazolyl, benzyl-triazolyl, pyridinylmethyl-triazolyl, cyanomethyl-triazolyl, dimethylaminomethyl-triazolyl, aminoethyl-triazolyl, dimethylaminoethyl-triazolyl, dimethylaminocarbonylmethyl-triazolyl, N-methylpiperidinyl-triazolyl, pyrrolidinylethyl-triazolyl, piperazinylethyl-triazolyl, morpholinylethyl-triazolyl, methyl-tetrazolyl, pyridinyl, methyl-pyridinyl, dimethyl-pyridinyl, ethoxy-pyridinyl, cyclopropylmethoxy-pyridinyl, pyridazinyl, chloro-pyridazinyl, pyrimidinyl, pyrazinyl, quinolinyl, isoquinolinyl and quinoxalinyl.

Specific values of $R^{22}$ include cyanophenyl, hydroxymethyl-phenyl, pyrazolyl, dimethyl-pyrazolyl, methyl-isoxazolyl, thiazolyl, methyl-thiazolyl, ethyl-thiazolyl, imidazolyl, methyl-imidazolyl, ethyl-imidazolyl, benzyl-imidazolyl, benzimidazolyl, methyl-oxadiazolyl, triazolyl, methyl-triazolyl, propyl-triazolyl, benzyl-triazolyl, pyridinylmethyl-triazolyl, cyanomethyl-triazolyl, dimethylaminomethyl-triazolyl, dimethylaminoethyl-triazolyl, dimethylaminocarbonylmethyl-triazolyl, morpholinylethyl-triazolyl, methyl-tetrazolyl, pyridinyl, methyl-pyridinyl, dimethyl-pyridinyl, ethoxy-pyridinyl, cyclopropylmethoxy-pyridinyl, pyridazinyl, chloro-pyridazinyl, pyrimidinyl, pyrazinyl, quinolinyl, isoquinolinyl and quinoxalinyl.

A favoured value of $R^{22}$ is methyl-triazolyl.

A particular subset of the compounds of formula I above is represented by the compounds of formula II, and pharmaceutically acceptable salts thereof:

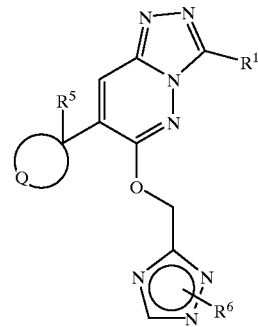

(II)

wherein $R^1$ is as defined with reference to formula I above;

Q represents the residue of a cyclopropyl, cyclobutyl, cyclopentyl or cyclohexyl ring;

$R^5$ represents hydrogen or methyl; and $R^6$ represents hydrogen or methyl.

In relation to formula II above, $R^1$ suitably represents phenyl.

In a favoured embodiment, Q suitably represents the residue of a cyclobutyl ring.

Suitably, $R^5$ represents hydrogen.

Suitably, $R^6$ represents methyl.

Specific GABA compounds of use in the present invention include:

3,7-diphenyl-6-(2-pyridyl)methyloxy- 1,2,4-triazolo[4,3-b]pyridazine;

7,8-dimethyl-3-phenyl-6-(2-pyridyl)methyloxy- 1,2,4-triazolo[4,3-b]pyridazine;

7-methyl-3-phenyl-6-(2-pyridyl)methyloxy-1,2,4-triazolo[4,3-b]pyridazine;
b 7-ethyl-3-phenyl-6-(2-pyridyl)methyloxy-1,2,4-triazolo[4,3-b]pyridazine;
8-methyl-3,7-diphenyl-6-(2-pyridyl)methyloxy- 1,2,4-triazolo[4,3-b]pyridazine;
3-phenyl-7-(piperidin-1-yl)-6-(pyridin-2-ylmethoxy)-1,2,4-triazolo[4,3-b]pyridazine;
3-phenyl-7-(pyridin-4-yl)-6-(pyridin-2-ylmethoxy)- 1,2,4-triazolo[4,3-b]pyridazine;
3-phenyl-6-(pyridin-2-ylmethoxy)-7-(thiophen-2-yl)-1,2,4-triazolo[4,3-b]pyridazine;
3-phenyl-6-(pyridin-2-ylmethoxy)-7-(thiophen-3-yl)-1,2,4-triazolo[4,3b]pyridazine;
6-(1-methyl-1H-1,2,4-triazol-3-ylmethoxy)-3,7-diphenyl-1,2,4-triazolo[4,3-b]pyridazine;
6-(2-methyl-2H-1,2,4-triazol-3-ylmethoxy)-3,7-diphenyl-1,2,4-triazolo[4,3-b]pyridazine;
3,7-diphenyl-6-(2H-1,2,4-triazol-3-ylmethoxy)-1,2,4-triazolo[4,3-b]pyridazine;
6-(2-methyl-2H-tetrazol-5-ylmethoxy)-3,7-diphenyl-1,2,4-triazolo[4,3-b]-pyridazine;
3,7-diphenyl-6-(2-propyl-2H-1,2,4-triazol-3-ylmethoxy)-1,2,4-triazolo[4,3-b]pyridazine;
3,7-diphenyl-6-(1-propyl-1H-1,2,4-triazol-3-ylmethoxy)-1,2,4-triazolo[4,3-b]pyridazine;
6-(1-methyl-1H-imidazol-4-ylmethoxy)-3,7-diphenyl-1,2,4-triazolo[4,3-b]pyridazine;
6-(3-methyl-3H-imidazol-4-ylmethoxy)-3,7-diphenyl-1,2,4-triazolo[4,3-b]pyridazine;
6-(4-methyl-4H-1,2,4-triazol-3-ylmethoxy)-3,7-diphenyl-1,2,4-triazolo[4,3-b]pyridazine;
6-(5-methyl-2H-1,2,4-triazol-3-ylmethoxy)-3,7-diphenyl-1,2,4-triazolo[4,3-b]pyridazine;
6-(3-methyl-3H-1,2,3-triazol-4-ylmethoxy)-3,7-diphenyl-1,2,4-triazolo[4,3-b]pyridazine;
3-(4-methoxyphenyl)-6-(1-methyl-1H-1,2,4-triazol-3-ylmethoxy)-7-phenyl-1,2,4-triazolo[4,3-b]pyridazine;
6-(3-methylpyridin-2-ylmethoxy)-3-phenyl-7-(piperidin-1-yl)-1,2,4-triazolo[4,3-b]pyridazine;
7-(morpholin-4-yl)-3-phenyl-6-(pyridin-2-ylmethoxy)-1,2,4-triazolo[4,3-b]pyridazine;
3-phenyl-7-(pyridin-3-yl)-6-(pyridin-2-ylmethoxy)-1,2,4-triazolo[4,3-b]pyridazine;
8-methyl-6-(2-methyl-2H-1,2,4-triazol-3-ylmethoxy)-3,7-diphenyl-1,2,4-triazolo[4,3-b]pyridazine;
6-(1-methyl-1H-1,2,4-triazol-3-ylmethoxy)-7-(morpholin-4-yl)-3-phenyl-1,2,4-triazolo[4,3-b]pyridazine;
6-(2-methyl-2H-1,2,4-triazol-3-ylmethoxy)-7-(morpholin-4-yl)-3-phenyl-1,2,4-triazolo[4,3-b]pyridazine;
7-cyclohexyl-6-(2-methyl-2H-1,2,4-triazol-3-ylmethoxy)-3-phenyl-1,2,4-triazolo[4,3-b]pyridazine;
7-cyclohexyl-6-(1-methyl-1H-1,2,4-triazol-3-ylmethoxy)-3-phenyl-1,2,4-triazolo [4,3-b]pyridazine;
7-cyclopentyl-6-(2-methyl-2H-1,2,4-triazol-3-ylmethoxy)-3-phenyl-1,2,4-triazolo[4,3-b]pyridazine;
8-methyl-6-(1-methyl-1H-1,2,4-triazol-3-ylmethoxy)-3,7-diphenyl-1,2,4-triazolo[4,3-b]pyridazine;
7-cyclobutyl-6-(1-methyl-1H-1,2,4-triazol-3-ylmethoxy)-3-phenyl-1,2,4-triazolo[4, 3-b]pyridazine;
7-tert-butyl-6-(2-methyl-2H-1,2,4-triazol-3-ylmethoxy)-3-phenyl-1,2,4-triazolo[4,3-b]pyridazine;
7-cyclobutyl-6-(2-methyl-2H-1,2,4-triazol-3-ylmethoxy)-3-phenyl-1,2,4-triazolo[4,3-b]pyridazine;
7-ethyl-6-(2-methyl-2H-1,2,4-triazol-3-ylmethoxy)-3-phenyl-1,2,4-triazolo[4,3-b]pyridazine;
7-tert-butyl-6-(1-methyl-1H-1,2,4-triazol-3-ylmethoxy)-3-phenyl-1,2,4-triazolo[4,3-b]pyridazine;
7-ethyl-6-(1-methyl-1H-1,2,4-triazol-3-ylmethoxy)-3-phenyl-1,2,4-triazolo[4,3-b]pyridazine;
7-methyl-6-(2-methyl-2H-1,2,4-triazol-3-ylmethoxy)-3-phenyl-1,2,4-triazolo[4,3-b]pyridazine;
7-(1-methylcyclobutyl)-6-(2-methyl-2H-1,2,4-triazol-3-ylmethoxy)-3-phenyl-1,2,4-triazolo[4,3-b]pyridazine;
7-methyl-6-(1-methyl-1H-1,2,4-triazol-3-ylmethoxy)-3-phenyl-1,2,4-triazolo[4,3-b]pyridazine;
7-cyclobutyl-3-phenyl-6-(2H-1,2,4-triazol-3-ylmethoxy)-1,2,4-triazolo[4,3-b]pyridazine;
7-cyclopentyl-6-(pyridin-2-ylmethoxy)-3-(thiophen-2-yl)-1,2,4-triazolo[4,3-b]pyridazine;
7-cyclopentyl-3-(2,4-difluorophenyl)-6-(1-methyl-1H-1,2,4-triazol-3-ylmethoxy)-1,2,4-triazolo[4,3-b]pyridazine;
7-cyclopentyl-6-(1-methyl-1H-1,2,4-triazol-3-ylmethoxy)-3-(thiophen-2-yl)-1,2,4-triazolo[4,3-b]pyridazine;
7-cyclopentyl-6-(2-methyl-2H-1,2,4-triazol-3-ylmethoxy)-3-(thiophen-2-yl)-1,2,4-triazolo[4,3-b]pyridazine;
7-cyclopentyl-6-(2-methyl-2H-1,2,4-triazol-3-ylmethoxy)-3-(pyridin-4-yl)-1,2,4-triazolo[4,3-b]pyridazine;
7-cyclopentyl-3-(2-fluorophenyl)-6-(1-methyl-1H-1,2,4-triazol-3-ylmethoxy)-1,2,4-triazolo[4,3-b]pyridazine;
7-cyclopentyl-3-(2-fluorophenyl)-6-(2-methyl-2H-1,2,4-triazol-3-ylmethoxy)-1,2,4-triazolo[4,3-b]pyridazine;
7-cyclopentyl-3-(2-fluorophenyl)-6-(pyridin-2-ylmethoxy)-1,2,4-triazolo[4,3-b]pyridazine;
7-cyclopentyl-3-(2,4-difluorophenyl)-6-(2-methyl-2H-1,2,4-triazol-3-ylmethoxy)-1,2,4-triazolo[4,3-b]pyridazine;
7-cyclopentyl-3-phenyl-6-(pyridin-2-ylmethoxy)-1,2,4-triazolo(4,3-b]pyridazine;
7-cyclopentyl-8-methyl-6-(2-methyl-2H-1,2,4-triazol-3-ylmethoxy)-3-phenyl-1,2,4-triazolo[4,3b]pyridazine;
7-cyclopentyl-3-phenyl-6-(2H-1,2,4-triazol-3-ylmethoxy)-1,2,4-triazolo[4,3-b]pyridazine;
3-(4-methylphenyl)-7-phenyl-6-(pyridin-2-ylmethoxy)-1,2,4-triazolo[4,3-b]pyridazine;
3-(4-methylphenyl)-6-(3-methylpyridin-2-ylmethoxy)-7-phenyl-1,2,4-triazolo[4,3-b]pyridazine;
6-(1-ethyl-1H-imidazol-2-ylmethoxy)-3-(4-methylphenyl)-7-phenyl-1,2,4-triazolo[4,3-b]pyridazine;
3-phenyl-6-(pyridin-2-ylmethoxy)-7-(thiomorpholin-4-yl)-1,2,4-triazolo[4,3-b]pyridazine;
6-[2-(4-methylthiazol-5-yl)ethoxy]-3,7-diphenyl-1,2,4-triazolo[4,3-b]pyridazine;
(±)-7-(2-methylpyrrolidin-1-yl)-3-phenyl-6-(pyridin-2-ylmethoxy)-1,2,4-triazolo [4,3-b]pyridazine;
6-(1-methyl-1H-1,2,4-triazol-3-ylmethoxy)-3-phenyl-7-(pyridin-4-yl)-1,2,4-triazolo[4,3-b]pyridazine;
7-cyclopentyl-6-(1-methyl-1H-1,2,4-triazol-3-ylmethoxy)-3-phenyl-1,2,4-triazolo[4,3-b]pyridazine;
7-isopropyl-6-(1-methyl-1H-1,2,4-triazol-3-ylmethoxy)-3-phenyl-1,2,4-triazolo[4,3b]pyridazine;
3-cyclopropyl-6-(1-methyl-1H-1,2,4-triazol-3-ylmethoxy)-7-phenyl-1,2,4-triazolo[4,3-b]pyridazine;
3-(2-fluorophenyl)-6-(2-methyl-2H-1,2,4-triazol-3-ylmethoxy)-7-phenyl-1,2,4-triazolo[4,3-b]pyridazine;
3-(2-fluorophenyl)-6-(1-methyl-1H-1,2,4-triazol-3-ylmethoxy)-7-phenyl-1,2,4-triazolo[4,3-b]pyridazine;
6-(1-methyl-1H-1,2,4-triazol-3-ylmethoxy)-7-phenyl-3-(thiophen-2-yl)-1,2,4-triazolo[4,3-b]pyridazine;
6-(1-methyl-1H-1,2,4-triazol-3-ylmethoxy)-7-phenyl-3-(pyridin-3-yl)-1,2,4-triazolo[4,3-b]pyridazine;
6-(2-methyl-2H-1,2,4-triazol-3-ylmethoxy)-7-phenyl-3-(thiophen-2-yl)-1,2,4-triazolo[4,3-b]pyridazine;
6-(2-methyl-2H-1,2,4-triazol-3-ylmethoxy)-7-phenyl-3-(pyridin-3-yl)-1,2,4-triazolo [4,3-b]pyridazine;
3-(furan-3-yl)-6-(1-methyl-1H-1,2,4-triazol-3-ylmethoxy)-7-phenyl-1,2,4-triazolo[4,3-b]pyridazine;

6-(1-methyl-1H-1,2,4-triazol-3-ylmethoxy)-7-phenyl-3-(thiophen-2-yl)-1,2,4-triazolo[4,3-b]pyridazine;
6-(5-methyl-1,2,4-oxadiazol-3-ylmethoxy)-3,7-diphenyl-1,2,4-triazolo[4,3-b]pyridazine;
7-phenyl-3-(thiophen-2-yl)-6-(2H-1,2,4-triazol-3-ylmethoxy)-1,2,4-triazolo[4,3-b]pyridazine;
3-(furan-2-yl)-6-(1-methyl-1H-1,2,4-triazol-3-ylmethoxy)-7-phenyl-1,2,4-triazolo[4,3-b]pyridazine;
6-(1-methyl-1H-1,2,4-triazol-3-ylmethoxy)-3-phenyl-7-(thiophen-3-yl)-1,2,4-triazolo[4,3-b]pyridazine;
6-(2-methyl-2H-1,2,4-triazol-3-ylmethoxy)-7-(thiophen-3-yl)-1,2,4-triazolo[4,3-b]pyridazine;
3-phenyl-7-(thiophen-3-yl)-6-(2H-1,2,4-triazol-3-ylmethoxy)-1,2,4-triazolo[4,3-b]pyridazine;
6-(2-methyl-2H-1,2,4-triazol-3-ylmethoxy)-3-phenyl-7-(thiophen-2-yl)-1,2,4-triazolo[4,3-b]pyridazine;
6-(1-methyl-1H-1,2,4-triazol-3-ylmethoxy)-3-phenyl-7-(thiophen-2-yl)-1,2,4-triazolo[4,3-b]pyridazine;
7-(furan-2-yl)-6-(2-methyl-2H-1,2,4-triazol-3-ylmethoxy)-3-phenyl-1,2,4-triazolo[4,3-b]pyridazine;
7-(furan-2-yl)-6-(1-methyl-1H-1,2,4-triazol-3-ylmethoxy)-3-phenyl-1,2,4-triazolo[4,3-b]pyridazine;
6-(3-methyl-1,2,4-oxadiazol-5-ylmethoxy)-3,7-diphenyl-1,2,4-triazolo[4,3-b]pyridazine;
3-(4-fluorophenyl)-6-(1-methyl-1H-1,2,4-triazol-3-ylmethoxy)-7-phenyl-1,2,4-triazolo[4,3-b]pyridazine;
3,7-diphenyl-6-(2H-1,2,3-triazol-4-ylmethoxy)-1,2,4-triazolo[4,3-b]pyridazine;
3,7-diphenyl-6-(pyrazin-2-ylmethoxy)-1,2,4-triazolo[4,3-b]pyridazine;
3-(4-methylphenyl)-6-(1-methyl-1H-1,2,4-triazol-3-ylmethoxy)-7-phenyl-1,2,4-triazolo[4,3-b]pyridazine;
6-(4-methylthiazol-2-ylmethoxy)-3,7-diphenyl-1,2,4-triazolo[4,3-b]pyridazine;
6-(5-methylthiazol-2-ylmethoxy)-3,7-diphenyl-1,2,4-triazolo[4,3-b]pyridazine;
3,7-diphenyl-6-(pyrimidin-4-ylmethoxy)-1,2,4-triazolo[4,3-b]pyridazine;
3,7-diphenyl-6-(pyridazin-3-ylmethoxy)-1,2,4-triazolo[4,3-b]pyridazine;
6-(1-methyl-1H-1,2,4-triazol-3-ylmethoxy)-7-(morpholin-4-yl)-3-(thiophen-2-yl)-1,2,4-triazolo[4,3-b]pyridazine;
3,7-diphenyl-6-(thiazol-4-ylmethoxy)-1,2,4-triazolo[4,3-b]pyridazine;
6-(5-methylisoxazol-3-ylmethoxy)-3,7-diphenyl-1,2,4-triazolo[4,3-b]pyridazine;
3-(3-fluorophenyl)-6-(1-methyl-1H-1,2,4-triazol-3-ylmethoxy)-7-(morpholin-4-yl)-1,2,4-triazolo[4,3-b]pyridazine;
3,7-diphenyl-6-(pyrimidin-2-ylmethoxy)-1,2,4-triazolo[4,3-b]pyridazine;
6-(2-methyl-2H-1,2,3-triazol-4-ylmethoxy)-3,7-diphenyl-1,2,4-triazolo[4,3-b]pyridazine;
7-(1-methylcyclobutyl)-6-(1-methyl-1H-1,2,4-triazol-3-ylmethoxy)-3-phenyl-1,2,4-triazolo[4,3-b]pyridazine;
7-isopropyl-6-(2-methyl-2H-1,2,4-triazol-3-ylmethoxy)-3-phenyl-1,2,4-triazolo[4,3-b]pyridazine;
7-tert-butyl-3-(2-fluorophenyl)-6-(1-methyl-1H-1,2,4-triazol-3-ylmethoxy)-1,2,4-triazolo[4,3-b]pyridazine;
7-cyclopentyl-3-(4-methoxyphenyl)-6-(2-methyl-2H-1,2,4-triazol-3-ylmethoxy)-1,2,4-triazolo[4,3-b]pyridazine;
7-(1-methylcyclopentyl)-6-(1-methyl-1H-1,2,4-triazol-3-ylmethoxy)-3-phenyl-1,2,4-triazolo[4,3-b]pyridazine;
7-(1-methylcyclopentyl)-6-(2-methyl-2H-1,2,4-triazol-3-ylmethoxy)-3-phenyl-1,2,4-triazolo[4,3-b]pyridazine;
7-cyclopentyl-3-(furan-2-yl)-6-(2-methyl-2H-1,2,4-triazol-3-ylmethoxy)-1,2,4-triazolo[4,3-b]pyridazine;
7-cyclopentyl-3-(furan-2-yl)-6-(1-methyl-1H-1,2,4-triazol-3-ylmethoxy)-1,2,4-triazolo[4,3-b]pyridazine;
3-(3,7-diphenyl-1,2,4-triazolo[4,3-b]pyridazin-6-yloxymethyl)-1,2,4-triazol-1-ylacetonitrile;
7-(1-methylcyclopropyl)-6-(2-methyl-2H-1,2,4-triazol-3-ylmethoxy)-3-phenyl-1,2,4-triazolo[4,3-b]pyridazine;
7-(1-methylcyclopropyl)-6-(1-methyl-1H-1,2,4-triazol-3-ylmethoxy)-3-phenyl-1,2,4-triazolo[4,3-b]pyridazine;
3-(3-fluorophenyl)-6-(1-methyl-1H-1,2,4-triazol-3-ylmethoxy)-7-phenyl-1,2,4-triazolo[4,3-b]pyridazine;
7-(1-methylcyclopentyl)-6-(3-methylpyridin-2-ylmethoxy)-3-phenyl-1,2,4-triazolo[4,3-b]pyridazine;
6-(1-methyl-1H-1,2,3-triazol-4-ylmethoxy)-3,7-diphenyl-1,2,4-triazolo[4,3-b]pyridazine;
3-(5-methylthiophen-2-yl)-6-(1-methyl-1H-1,2,4-triazol-3-ylmethoxy)-7-phenyl-1,2,4-triazolo[4,3-b]pyridazine;
2-[3-(3,7-diphenyl-1,2,4-triazolo[4,3-b]pyridazin-6-yloxymethyl)-1,2,4-triazol-1-yl]-N,N-dimethylacetamide;
3,7-diphenyl-6-[1-(pyridin-2-ylmethyl)-1H-1,2,4-triazol-3-ylmethoxy]-1,2,4-triazolo[4,3-b]pyridazine;
6-(1-benzyl-1H-1,2,4-triazol-3-ylmethoxy)-3,7-diphenyl-1,2,4-triazolo[4,3-b]pyridazine;
2-[5-(3,7-diphenyl-1,2,4-triazolo[4,3-b]pyridazin-6-yloxymethyl)-1,2,4-triazol-1-yl]acetamide;
N-[2-[3-(3,7-diphenyl-1,2,4-triazolo[4,3-b]pyridazin-6-yloxymethyl)-1,2,4-triazol-1-yl]ethyl]-N,N-dimethylamine;
3,7-diphenyl-6-(pyrimidin-5-ylmethoxy)-1,2,4-triazolo[4,3-b]pyridazine;
6-[1-(2-(morpholin-4-yl)-ethyl)-1H-1,2,4-triazol-3-ylmethoxy]-3,7-diphenyl-1,2,4-triazolo[4,3-b]pyridazine;
6-(2-methyl-2H-1,2,4-triazol-3-ylmethoxy)-3-phenyl-7-(pyrrolidin-1-yl)-1,2,4-triazolo[4,3-b]pyridazine;
7-(5-chlorothiophen-2-yl)-6-(2-methyl-2H-1,2,4-triazol-3-ylmethoxy)-3-phenyl-1,2,4-triazolo[4,3-b]pyridazine;
7-(5-chlorothiophen-2-yl)-6-(1-methyl-1H-1,2,4-triazol-3-ylmethoxy)-3-phenyl-1,2,4-triazolo[4,3-b]pyridazine;
6-(1H-benzimidazol-2-ylmethoxy)-3-(2,4-difluorophenyl)-7-(1-methylcyclopentyl)-1,2,4-triazolo[4,3-b]pyridazine;
2-[3-(3,7-diphenyl-1,2,4-triazolo[4,3-b]pyridazin-6-yloxymethyl)-1,2,4-triazol-1-yl]ethylamine;
3,7-diphenyl-6-[1-(2-(pyrrolidin-1-yl)ethyl)-1H-1,2,4-triazol-3-ylmethoxy]-1,2,4-triazolo[4,3-b]pyridazine;
6- [1-(1-methylpiperidin-4-yl)-1H-1,2,4-triazol-3-ylmethoxy]-3,7-diphenyl-1,2,4-triazolo[4,3-b]pyridazine;
3,7-diphenyl-6-[1-(2-(piperazin-1-yl)ethyl)-1H-1,2,4-triazol-3-ylmethoxy]-1,2,4-triazolo[4,3-b]pyridazine;
7-(1-methylcyclopentyl)-6-(2-methyl-2H-1,2,4-triazol-3-ylmethoxy)-3-(2,4-difluorophenyl)-1,2,4-triazolo[4,3-b]pyridazine;
7-(cyclobut-1-enyl)-6-(2-methyl-2H-1,2,4-triazol-3-ylmethoxy)-3-phenyl-1,2,4-triazolo[4,3-b]pyridazine;
7-(furan-3-yl)-6-(1-methyl-1H-1,2,4-triazol-3-ylmethoxy)-3-phenyl-1,2,4-triazolo[4,3-b]pyridazine;
N,N-diethyl-N-[6-(1-methyl-1H-1,2,4-triazol-3-ylmethoxy)-3-phenyl-1,2,4-triazolo [4,3-b]pyridazin-7-yl]amine;
7-(1-methylcyclopentyl)-6-(1-methyl-1H-1,2,4-triazol-3-ylmethoxy)-3-(2,4-difluorophenyl)-1,2,4-triazolo[4,3-b]pyridazine;
7-(1,1-dimethylpropyl)-6-(1-methyl-1H-1,2,4-triazol-3-ylmethoxy)-3-phenyl-1,2,4-triazolo[4,3-b]pyridazine;
6-(2-methyl-2H-1,2,4-triazol-3-ylmethoxy)-3-(4-fluorophenyl)-7-(thiophen-3-yl)-1,2,4-triazolo[4,3-b]pyridazine;
6-(1-methyl-1H-1,2,4-triazol-3-ylmethoxy)-3-(4-fluorophenyl)-7-(thiophen-3-yl)-1,2,4-triazolo[4,3-b]pyridazine;

6-(2-methyl-2H-1,2,4-triazol-3-ylmethoxy)-3-(2-fluorophenyl)-7-(thiophen-3-yl)1,2,4-triazolo[4,3-b]pyridazine;

3-(2-fluorophenyl)-7-(1-methylcyclobutyl)-6-(2-methyl-2H-1,2,4-triazol-3-ylmethoxy)-1,2,4-triazolo[4,3-b]pyridazine;

3-(2-fluorophenyl)-7-(1-methylcyclobutyl)-6-(1-methyl-1H-1,2,4-triazol-3-ylmethoxy)-1,2,4-triazolo[4,3-b]pyridazine;

6-(1-methyl-1H-1,2,4-triazol-3-ylmethoxy)-3(2-fluorophenyl)-7-(thiophen-3-yl)-1,2,4-triazolo[4,3-b]pyridazine;

8-methyl-7-(1-methylcyclobutyl)-6-(1-methyl-1H-1,2,4-triazol-3-ylmethoxy)-3-phenyl-1,2,4-triazolo[4,3-b]pyridazine;

8-methyl-7-(1-methylcyclobutyl)-6-(2-methyl-2H-1,2,4-triazol-3-ylmethoxy)-3-phenyl-1,2,4-triazolo[4,3-b]pyridazine;

6-(1-methyl-1H-1,2,4-triazol-3-ylmethoxy)-3-phenyl-7-(pyrrolidin-1-yl)-1,2,4-triazolo[4,3-b]pyridazine;

7-cyclobutyl-8-methyl-6-(2-methyl-2H-1,2,4-triazol-3-ylmethoxy)-3-phenyl-1,2,4-triazolo[4,3-b]pyridazine;

7-cyclobutyl-8-methyl-6-(1-methyl-1H-1,2,4-triazol-3-ylmethoxy)-3-phenyl-1,2,4-triazolo[4,3-b]pyridazine;

7-(1-methylcyclopentyl)-6-(2-methyl-2H-1,2,4-triazol-3-ylmethoxy)-3-(2-fluorophenyl)-1,2,4-triazolo[4,3-b]pyridazine;

7-(1-methylcyclopentyl)-6-(1-methyl 1H-1,2,4-triazol-3-ylmethoxy)-3-(2-fluorophenyl)-1,2,4-triazolo[4,3-b]pyridazine;

and salts and prodrugs thereof

Suitable serotonin reuptake inhibitors of use in the present invention include: fluoxetine, fluvoxamine, paroxetine and sertraline, and pharmaceutically acceptable salts thereof.

The present invention also provides a pharmaceutical product comprising an SSRI and a non-sedating anxiolytic compound which is a modulator of the benzodiazepine binding site of the human $GABA_A$ receptor, having a binding affinity ($K_i$) for the α3 subunit of the human $GABA_A$ receptor of 10 nM or less, which elicits at least a 40% potentiation of the GABA $EC_{20}$ response in stably transfected recombinant cell lines expressing the α3 subunit of the human $GABA_A$ receptor, and which elicits at most a 30% potentiation of the GABA $EC_{20}$ response in stably transfected cell lines expressing the α1 subunit of the human $GABA_A$ receptor for simultaneous, separate or sequential administration.

In this aspect of the invention, the binding affinity ($K_i$) of compounds for the α3 subunit of the human $GABA_A$ receptor is conveniently as measured in the assay described hereinbelow. The α3 subunit binding affinity ($K_i$) of compounds fulfilling this aspect of the invention is 10 nM or less, preferably 2 nM or less, and more preferably 1 nM or less.

In this aspect of the invention, the potentiation of the GABA $EC_{20}$ response in stably transfected cell lines expressing the α3 and α1 subunits of the human $GABA_A$ receptor can conveniently be measured by procedures analogous to the protocol described in Wafford et al., *Mol. Pharmacol.*, 1996, 60, 670–678. The procedure will suitably be carried out utilising cultures of stably transfected eukaryotic cells, typically of stably transfected mouse Ltk– fibroblast cells.

The GABA compounds of use this aspect of the invention will elicit at least a 40%, preferably at least a 50%, and more preferably at least a 60%, potentiation of the GABA $EC_{20}$ response in stably transfected recombinant cell lines expressing the α3 subunit of the human $GABA_A$ receptor.

Moreover, the compounds fulfilling this aspect of the invention will elicit at most a 30%, preferably at most a 20%, and more preferably at most a 10%, potentiation of the GABA $EC_{20}$ response in stably transfected recombinant cell lines expressing the α1 subunit of the human $GABA_A$ receptor.

The GABA compounds of use in this aspect of the invention exhibit anxiolytic activity, as demonstrated by a positive response in the elevated plus maze and conditioned suppression of drinking tests (cf. Dawson et al., *Psychopharmacology*, 1995, 121, 109–117). Moreover, the compounds fulfilling this aspect of the invention are substantially non-sedating, as confirmed by an appropriate result obtained from the response sensitivity (chain-pulling) test (cf. Bayley et al., *J. Psychopharmacol.*, 1996, 10, 206–213).

The GABA compounds of use in this aspect of the invention also exhibit anticonvulsant activity. This is demonstrated by their ability to block pentylenetetrazole-induced seizures in rats and mice, following a protocol analogous to that described by Bristow et al. in *J. Pharmacol. Exp. Ther.*, 1996, 279, 492–501.

In order to elicit their behavioural effects, the compounds of use in this aspect of the invention will be brain-penetrant; in other words, these compounds will be capable of crossing the so-called "blood-brain barrier". Preferably, the compounds fulfilling this aspect of the invention will be capable of exerting their beneficial therapeutic action following administration by the oral route.

A representative GABA compound of use in this aspect of the invention is 7-cyclobutyl-6-(2-methyl-2H-1,2,4-triazol-3-ylmethoxy)-3-phenyl-1,2,4-triazolo[4,3-b]pyridazine.

Suitable SSRIs are as indicated above.

Pharmaceutical compositions of use in the present invention will comprise one or both active compound(s) in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. Typical unit dosage forms contain from 1 to 100 mg, for example 1, 2, 5, 10, 25, 50 or 100 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

When administered in combination, either as a single or as separate pharmaceutical composition(s), the $GABA_A$ $\alpha 2/3$ agonist and the SSRI are presented in a ratio which is consistent with the manifestation of the desired effect. In particular, the ratio by weight of the $GABA_A$ $\alpha 2/3$ agonist and the SSRI will suitably be between 0.001 to 1 and 1000 to 1, and especially between 0.01 to 1 and 100 to 1.

A suitable dosage level for the $GABA_A$ $\alpha 2/3$ agonist is about 0.05 to 1500 mg per day, preferably about 0.25 to 1500 mg per day, and especially about 0.25 to 500 mg per day. The compounds may be administered on a regimen of up to 6 times per day, preferably 1 to 4 times per day, especially 2 times per day and most especially once daily.

A suitable dosage level for the SSRI is about 0.5 to 1500 mg per day, preferably about 2.5 to 1000 mg per day, and especially about 2.5 to 500 mg per day. The compounds may be administered on a regimen of up to 6 times per day, preferably 1 to 4 times per day, especially 2 times per day and most especially once daily.

It will be appreciated that the amount of the $GABA_A$ $\alpha 2/3$ agonist and the SSRI required for use in the treatment or prevention of depression and/or anxiety will vary not only with the particular compounds or compositions selected but also with the route of administration, the nature of the condition being treated, and the age and condition of the patient, and will ultimately be at the discretion of the patient's physician or pharmacist.

As used herein the term "patient" includes animals of economic importance such as bovine, ovine, and porcine animals, especially those that produce meat, as well as domestic animals (e.g. cats and dogs), sports animals (e.g. horses), zoo animals, and humans, the latter being preferred.

The compounds of formula I can be prepared as described in WO-A-9804559.

The GABA compounds of use with this invention potently inhibit the binding of [$^3$H]-flumazenil to the benzodiazepine binding site of human $GABA_A$ receptors containing the $\alpha 2$ or $\alpha 3$ subunit stably expressed in Ltk$^-$ cells.

Reagents

Phosphate buffered saline (PBS).

Assay buffer: 10 mM $KH_2PO_4$, 100 mM KCl, pH 7.4 at room temperature.

[$^3$H]-Flumazenil (18 nM for $\alpha 1\beta 3\gamma 2$ cells; 18 nM for $\alpha 2\beta 3\gamma 2$ cells; 10 nM for $\alpha 3\beta 3\gamma 2$ cells) in assay buffer.

Flunitrazepam 100 $\mu$M in assay buffer.

Cells resuspended in assay buffer (1 tray to 10 ml).

Harvesting Cells

Supernatant is removed from cells. PBS (approximately 20 ml) is added. The cells are scraped and placed in a 50 ml centrifuge tube. The procedure is repeated with a further 10 ml of PBS to ensure that most of the cells are removed. The cells are pelleted by centrifuging for 20 min at 3000 rpm in a benchtop centrifuge, and then frozen if desired. The pellets are resuspended in 10 ml of buffer per tray (25 cm×25 cm) of cells.

Assay

Can be carried out in deep 96-well plates or in tubes. Each tube contains:

300 $\mu$l of assay buffer.

50 $\mu$l of [$^3$H]-flumazenil (final concentration for $\alpha 1\beta 3\gamma 2$: 1.8 nM; for $\alpha 2\beta 3\gamma 2$: 1.8 nM; for $\alpha 3\beta 3\gamma 2$: 1.0 nM).

50 $\mu$l of buffer or solvent carrier (e.g. 10% DMSO) if compounds are dissolved in 10% DMSO (total); test compound or flunitrazepam (to determine non-specific binding), 10 $\mu$M final concentration.

100 $\mu$l of cells.

Assays are incubated for 1 hour at 40° C., then filtered using either a Tomtec or Brandel cell harvester onto GF/B filters followed by 3×3 ml washes with ice cold assay buffer. Filters are dried and counted by liquid scintillation counting. Expected values for total binding are 3000–4000 dpm for total counts and less than 200 dpm for non-specific binding if using liquid scintillation counting, or 1500–2000 dpm for total counts and less than 200 dpm for non-specific binding if counting with meltilex solid scintillant. Binding parameters are determined by non-linear least squares regression analysis, from which the inhibition constant $K_i$ can be calculated for each test compound. The compounds of use in the present invention have a $K_i$ value for displacement of [$^3$H]-flumazenil from the $\alpha 2$ and/or $\alpha 3$ subunit of the human $GABA_A$ receptor of 100 nM or less when tested in the above assay.

What is claimed is:

1. A pharmaceutical product comprising an SSRI and a non-sedating anxiolytic compound which is a modulator of the benzodiazepine binding site of the human $GABA_A$ receptor, having a binding affinity ($K_i$) for the $\alpha 3$ subunit of the human $GABA_A$ receptor of 10 nM or less, which elicits at least a 40% potentiation of the GABA $EC_{20}$ response in stably transfected recombinant cell lines expressing the $\alpha 3$ subunit of the human $GABA_A$ receptor, and which elicits at most a 30% potentiation of the GABA $EC_{20}$ response in stably transfected cell lines expressing the $\alpha 1$ subunit of the human $GABA_A$ receptor for simultaneous, separate or sequential administration.

2. A pharmaceutical product according to claim 1 wherein the SSRI is fluoxetine, paroxetine or sertraline or a pharmaceutically acceptable salt thereof.

3. A pharmaceutical product comprising an SSRI and a compound of formula I or a salt thereof:

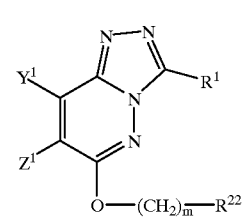

(I)

wherein $Y^1$ represents hydrogen or methyl;

$Z^1$ represents $C_{1-6}$alkyl, $C_{3-7}$cycloalkyl, $C_{4-7}$cycloalkenyl, aryl, $C_{3-7}$heterocycloalkyl, heteroaryl or di($C_{1-6}$)

alkylamino, any of which groups may be optionally substituted with one or two independent $C_{1-6}$alkyl, aryl($C_{1-6}$)alkyl, pyridyl($C_{1-6}$)alkyl, halogen, halo($C_{1-6}$) alkyl, cyano, cyano($C_{1-6}$)alkyl, hydroxy, hydroxymethyl, $C_{1-6}$alkoxy, $C_{3-7}$cycloalkyl($C_{1-6}$) alkoxy, $C_{3-7}$ cycloalkoxy, amino($C_{1-6}$)alkyl, di($C_{1-6}$) alkylamino($C_{1-6}$)alkyl, di($C_{1-6}$)alkylaminocarbonyl ($C_{1-6}$)alkyl, N-($C_{1-6}$)alkylpiperdinyl, pyrrolidinyl($C_{1-6}$) alkyl, piperazinyl($C_{1-6}$)alkyl, morpholinyl($C_{1-6}$)alkyl, di($C_{1-6}$)alkylmorpholinyl($C_{1-6}$)alkyl or imidazolyl($C_{1-6}$)alkyl substituents;

$R^1$ represents C3–7cycloalkyl, phenyl, furyl, thienyl or pyridinyl, any of which groups may be optionally substituted with one or two independent $C_{1-6}$alkyl, aryl($C_{1-6}$)alkyl, pyridyl($C_{1-6}$)alkyl, halogen, halo($C_{1-6}$) alkyl, cyano, cyano($C_{1-6}$)alkyl, hydroxy, hydroxymethyl, $C_{1-6}$alkoxy, $C_{3-7}$cycloalkyl($C_{1-6}$) alkoxy, $C_{3-7}$ cycloalkoxy, amino($C_{1-6}$)alkyl, di($C_{1-6}$) alkylamino($C_{1-6}$)alkyl, di($C_{1-6}$)alkylaminocarbonyl ($C_{1-6}$)alkyl, N-($C_{1-6}$)alkylpiperidinyl, pyrrolidinyl($C_{1-6}$)alkyl, piperazinyl($C_{1-6}$)alkyl, morpholinyl($C_{1-6}$) alkyl, di($C_{1-6}$)alkylmorpholinyl($C_{1-6}$)alkyl or imidazolyl($C_{1-6}$)alkyl substituents;

m is 1 or 2; and $R^{22}$ represents aryl or heteroaryl, either of which groups may be optionally substituted with one or two independent $C_{1-6}$alkyl, aryl($C_{1-6}$)alkyl, pyridyl($C_{1-6}$)alkyl, halogen, halo($C_{1-6}$)alkyl, cyano, cyano($C_{1-6}$)alkyl, hydroxy, hydroxymethyl, $C_{1-6}$alkoxy, $C_{3-7}$cycloalkyl ($C_{1-6}$)alkoxy, $C_{3-7}$ cycloalkoxy, amino($C_{1-6}$)alkyl, di($C_{1-6}$)alkylamino($C_{1-6}$)alkyl, di($C_{1-6}$) alkylaminocarbonyl($C_{1-6}$)alkyl, N-($C_{1-6}$) alkylpiperidinyl, pyrrolidinyl($C_{1-6}$)alkyl, piperazinyl ($C_{1-6}$)alkyl, morpholinyl($C_{1-6}$)alkyl, di($C_{1-6}$) alkylmorpholinyl($C_{1-6}$)alkyl or imidazolyl($C_{1-6}$)alkyl substituents.

4. A pharmaceutical product according to claim 3 wherein SSRI is fluoxetine, paroxetine or sertraline or a pharmaceutically acceptable salt thereof.

5. The pharmaceutical product according to claim 3 wherein $Y^1$ represents hydrogen.

6. The pharmaceutical product according to claim 3 wherein $Z^1$ represents methyl, ethyl, isopropyl, tert-butyl, 1,1-dimethylpropyl, methyl-cyclopropyl, cyclobutyl, methyl-cyclobutyl, cyclopentyl, methyl-cyclopentyl, cyclohexyl, cyclobutenyl, phenyl, pyrrolidinyl, methyl-pyrrolidinyl, piperidinyl, morpholinyl, thiomorpholinyl, pyridinyl, furyl, thienyl, chloro-thienyl, or diethylamino.

7. The pharmaceutical product according to claim 3 wherein $R^1$ represents cyclopropyl, phenyl, methylphenyl, fluorophenyl, difluorophenyl, methoxyphenyl, furyl, thienyl, methyl-thienyl, or pyridinyl.

8. The pharmaceutical product according to claim 3 in which m is 1.

9. The pharmaceutical product according to claim 3 wherein $R^{22}$ represents cyanophenyl, hydroxymethyl-phenyl, pyrazolyl, dimethyl-pyrazolyl, methyl-isoxazolyl, thiazolyl, methyl-thiazolyl, ethyl-thiazolyl, imidazolyl, methyl-imidazolyl, ethyl-imidazolyl, benzyl-imidazolyl, benzimidazolyl, methyl-oxadiazolyl, triazolyl, methyl-triazolyl, propyl-triazolyl, benzyl-triazolyl, pyridinylmethyl-triazolyl, cyanomethyl-triazolyl, dimethylaminomethyl-triazolyl, aminoethyl-triazolyl, dimethylaminoethyl-triazolyl, dimethylaminocarbonylmethyl-triazolyl, N-methylpiperidinyl-triazolyl, pyrrolidinylethyl-triazolyl, piperazinylethyl-triazolyl, morpholinylethyl-triazolyl, methyl-tetrazolyl, pyridinyl, methyl-pyridinyl, dimethyl-pyridinyl, ethoxy-pyridinyl, cyclopropylmethoxy-pyridinyl, pyridazinyl, chloropyridazinyl, pyrimidinyl, pyrazinyl, quinolinyl, isoquinolinyl or quinoxalinyl.

10. The pharmaceutical product according to claim 9 wherein $R^{22}$ represents methyl-triazolyl.

11. The pharmaceutical product according to claim 3 comprising an SSRI and a compound of formula II or a salt thereof:

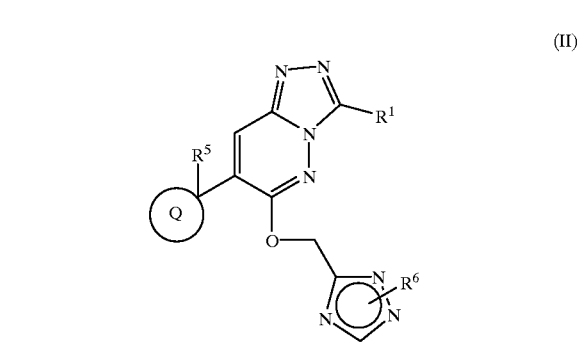

(II)

wherein

Q represents cyclopropyl, cyclobutyl, cyclopentyl, or cyclohexyl;

$R^5$ represents hydrogen or methyl; and $R^6$ represents hydrogen or methyl.

12. The pharmaceutical product according to claim 11 wherein Q represents cyclobutyl.

13. The pharmaceutical product according to claim 11 wherein $R^5$ represents hydrogen.

14. The pharmaceutical product according to claim 11 wherein $R^6$ represents methyl.

* * * * *